United States Patent
Abe et al.

(10) Patent No.: US 6,225,056 B1
(45) Date of Patent: May 1, 2001

(54) SOLID PHASES FOR TARGET NUCLEIC ACID DETECTION, PROCESS FOR PRODUCTION THEREOF, AND METHOD OF TARGET NUCLEIC ACID DETECTION

(75) Inventors: Satoshi Abe, Shizuoka; Yoshihiro Sato, Aichi, both of (JP)

(73) Assignee: Laboratory of Molecular Biophotonics, Hamakita (JP)

(*) Notice: Subject to any disclaimer, the term of this patent is extended or adjusted under 35 U.S.C. 154(b) by 0 days.

(21) Appl. No.: 09/065,058

(22) PCT Filed: Sep. 12, 1997

(86) PCT No.: PCT/JP97/03232

§ 371 Date: Apr. 27, 1998

§ 102(e) Date: Apr. 27, 1998

(87) PCT Pub. No.: WO98/11210

PCT Pub. Date: Mar. 19, 1998

(30) Foreign Application Priority Data

Sep. 13, 1996 (JP) .................................................. 8-243720

(51) Int. Cl.[7] ............................ C12Q 1/68; C07H 21/02; C07H 21/04; C12N 15/00
(52) U.S. Cl. ............................ 435/6; 536/23.1; 536/24.3; 935/76; 935/77; 935/78
(58) Field of Search ...................... 435/6, 91.2; 536/22.1, 536/23.1, 24.3; 935/76, 77, 78

(56) References Cited

U.S. PATENT DOCUMENTS

| | | | |
|---|---|---|---|
| 5,512,439 | * | 4/1996 | Hornes et al. ............................ 435/6 |
| 5,631,134 | * | 5/1997 | Cantor ...................................... 435/6 |
| 5,641,658 | * | 6/1997 | Adams et al. ........................ 435/91.2 |
| 5,792,607 | * | 8/1998 | Backman et al. ......................... 435/6 |
| 5,854,033 | * | 12/1998 | Lizardi ................................. 435/91.2 |
| 5,866,337 | * | 2/1999 | Schon ........................................ 435/6 |
| 5,869,252 | * | 2/1999 | Bouma et al. ........................... 435/6 |
| 5,871,928 | * | 2/1999 | Foder et al. .............................. 435/6 |
| 6,025,139 | * | 2/2000 | Yager et al. .............................. 435/6 |
| 6,027,889 | * | 2/2000 | Barany et al. ............................ 435/6 |
| 6,133,436 | * | 10/2000 | Köster et al. ........................ 536/24.3 |

FOREIGN PATENT DOCUMENTS

WO95/22623 * 8/1995 (WO) .
WO97/31256 * 8/1997 (WO) .

OTHER PUBLICATIONS

Barany, F., Genetic Disease Detection and DNA Amplification using Cloned Thermostable Ligase. PNAS, USA 88 : 189–193 (1991).*

Matthews et al., Analytical Strategies for the Use of DNA Probes. Analytical Biochemistry 169 :1–25 (1988).*

Saiki et al., Analysis of Enzymatically Amplified Beta–globin and HLA–DQalpha DNA with Allele–specific Oligonucleotide Probes. Science 324 : 163–166 (1986).*

Nickerson et al., "Automated DNA diagnosis using and ELISA–based oligonucleotide ligation assay", *Proc. Natl. Acad. Sci. USA*, 87, 8923–8927 (1990).

Nisson et al., "Padlock Probes: Circularizing Oligonucleotides for Localized DNA Detection", *Science*, 265, 2085–2088 (1994).

Schlief et al., "Hybridization of Nucleic Acid" 172–173 (summary). (No date).

* cited by examiner

*Primary Examiner*—Ethan Whisenant
(74) *Attorney, Agent, or Firm*—Leydig, Voit & Mayer, Ltd.

(57) ABSTRACT

A solid phase comprising at least one pair of probes which are capable of sequentially hybridizing with a particular target nucleic acid sequence is provided. The probe pair(s) are immobilized on the solid phase through a linker portion wherein they occupy a restricted spatial arrangement such that they can be ligated by an enzyme when the they sequentially hybridize to a selected target sequence. In addition a method wherein the solid phase is utilized to detection a target nucleic acid is disclosed.

12 Claims, 8 Drawing Sheets

TARGET NUCLEIC ACID
LIGASE REACTION

D→A INTERACTION

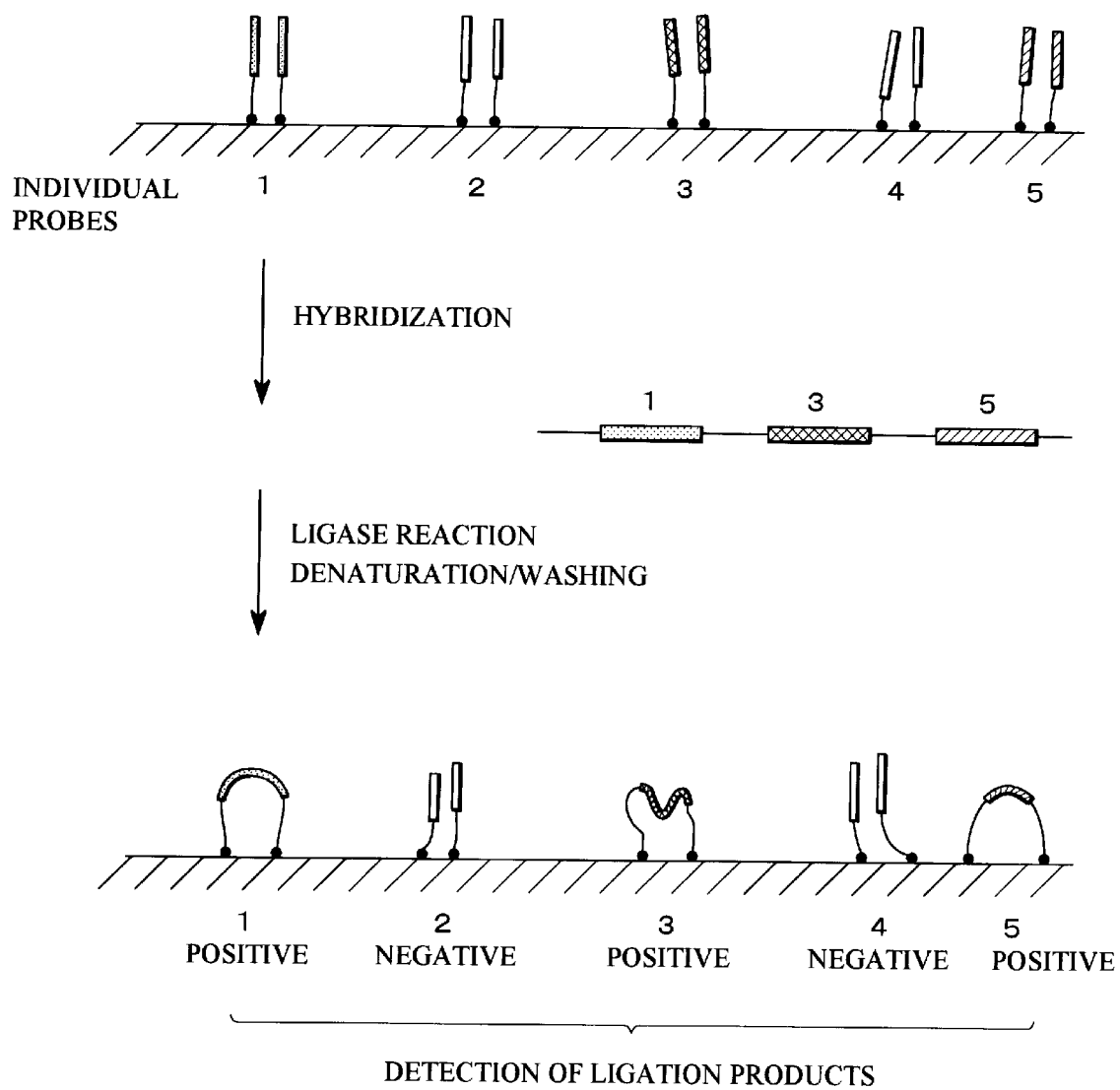

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (ix) FEATURE: 3'-end is labeled with biotin and 5'-end phosphorylated (xi) SEQUENCE DESCRIPTION: SEQ ID NO: 1:

TAGTGGATCC CCCGGGCTGC      20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (ix) FEATURE: 5'-end is labeled with biotin (xi) SEQUENCE DESCRIPTION: SEQ ID NO: 2:

GGTGGCGGCC GCTCTAGAAC                                                          20

(2) INFORMATION FOR SEQ ID NO: 3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

GCAGCCCGGG GGATCCACTA GTTCTAGAGC GGCCGCCACC                                     40

(2) INFORMATION FOR SEQ ID NO: 4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE: 3'-end is labeled with biotin and 5'-end
         phosphorylated (xi) SEQUENCE DESCRIPTION: SEQ ID NO: 4:

TAGTGGATCC CCCGGGCTGC AGGAATTCGA TATCAAGCTT                                     40

(2) INFORMATION FOR SEQ ID NO: 5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (ix) FEATURE: 5'-end is labeled with biotin (xi) SEQUENCE DESCRIPTION: SEQ ID NO: 5:

GCGAATTGGA GCTCCACCGC GGTGGCGGCC GCTCTAGAAC                                     40

(2) INFORMATION FOR SEQ ID NO: 6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GCAGCCCGGG GGATCCACTA AGTTCTAGAG CGGCCGCCAC C                                   41

(2) INFORMATION FOR SEQ ID NO: 7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

GCAGCCCGGG GGATCCACTG TTCTAGAGCG GCCGCCACC 39

(2) INFORMATION FOR SEQ ID NO: 8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

GCAGCCCGGG GGATCCACTA TTCTAGAGCG GCCGCCACC 39

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GCAGCCCGGG GGATCCACTT GTTCTAGAGC GGCCGCCACC 40

(2) INFORMATION FOR SEQ ID NO: 10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GCAGCCCGGG GGATCCACTG GTTCTAGAGC GGCCGCCACC 40

(2) INFORMATION FOR SEQ ID NO: 11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

GCAGCCCGGG GGATCCACTC GTTCTAGAGC GGCCGCCACC 40

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

GCAGCCCGGG GGATCCACTA ATTCTAGAGC GGCCGCCACC 40

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

GCAGCCCGGG GGATCCACTA TTTCTAGAGC GGCCGCCACC            40

(2) INFORMATION FOR SEQ ID NO: 14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

GCAGCCCGGG GGATCCACTA CTTCTAGAGC GGCCGCCACC            40

(2) INFORMATION FOR SEQ ID NO: 15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GCAGCCCGGG GGATCCACTA GTTCTAGAGC GGCCGCCACC GCGGTGGAGC TCCAATTCGC    60

(2) INFORMATION FOR SEQ ID NO: 16:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (ix) FEATURE: 5'-end is phosphorylated (xi) SEQUENCE DESCRIPTION: SEQ ID NO: 16:

GCGGTGGAGC TCCAATTCGC TTTTTTTTTT TTTTTTTTTT TTTTTTTTTT TTTTTTTTTT    60

TTTTTTTTTT GTTCTAGAGC GGCCGCCACC                                  90

SOLID PHASES FOR TARGET NUCLEIC ACID DETECTION, PROCESS FOR PRODUCTION THEREOF, AND METHOD OF TARGET NUCLEIC ACID DETECTION

DESCRIPTION

1. Technical Field

This invention relates to solid phases for the detection of target nucleic acids, their preparation methods, and methods of detecting target nucleic acids employing the same.

2. Background Art

With the advent of research developments in recent years, a variety of biological information has come to being derivable from gene sequences. Consequently, detection of the genes (which correspond to the specified polynucleotide sequences of target nucleic acids) has enabled the diagnosis of diseases, susceptibility against drugs, compatibility in organ transplantation and the like in the medical field; it has enabled the detection and identification of diverse pathogens responsible for food poisoning in food science.

In order to detect such specified polynucleotide sequences, hybridization methods are generally performed using probes that comprise sequences complementary to those to be detected. Since the sequences to be detected vary widely in accordance with the purposes of detection, probes having a variety of sequences in accordance with those purposes are employed in the detection. Also, there may be cases where reactions with from tens to a few hundreds of probes have to be examined at one time to confirm the presence of plural sequences in a single sample.

Regarding the simple technique of examining reaction with a large number of probes as described, generally known is a method to use a solid phase such as a filter on which probes have been immobilized. FIG. 1 schematically illustrates a method where a probe immobilized on the solid phase is used to hybridize to the target nucleic acid and to detect it. This method arranges plural probes on a single solid phase at certain distances; thereby, it allows the simultaneous detection of the reaction with many probes at one time even if a small amount of the sample is used. However, the method employing probes immobilized on the solid phase generally suffers from low efficiencies in reaction with the target nucleic acids because the probes are subjected to restrictions in their movement due to the immobilization, and in addition, it has a difficulty in detection with high sensitivity because background signals arising from the nonspecific adsorption of the sample to the solid phase are generated. Furthermore, mutual binding between nucleic acids themselves by virtue of hybridization takes place even if there are a few mismatches between the sequences and, as a result, the poor ability to recognize sequences is named as a problem common in the hybridization methods.

The oligonucleotide ligation assay is disclosed in Proc. Natl. Acad. Sci. USA (1990) 87, 8923–8927, which is a method to improve the sensitivity and the ability to recognize sequences in the hybridization methods. This method is schematically shown in FIG. 2. Two probes are reacted with the target nucleic acid: in the two probes a group binding to the solid phase is introduced into one of the two nucleic acids capable of sequentially hybridizing with a target sequence and a group useful for detection is introduced into the other. Then only the correctly hybridized probe is ligated by addition of a ligase. Differing from the methods where probes have been immobilized in advance, these reactions are very efficient since they are conducted in a liquid phase where molecules freely move; further, they enjoy higher sequence recognition than the detection methods solely relying on hybridization, since the ligation reaction by the action of ligase proceeds in such a strict manner that it does not take place if there is disparity in only one base. The probe ligated by the action of ligase can easily be separated by being bound to the solid phase and is detected through the group that has been introduced for the purpose of detection. However, where the sequences to be detected vary diversely, this method compels a technician himself to add different probes depending on the sequences to be detected and, as a result, gives unnecessary tension to the technician, thus likely inducing erroneous additions or the like. Moreover, when plural probes are reacted at the same time, it is difficult to identify as to which sequences correspond to the probes having been detected.

Accordingly, there is a need for the simple method which uses probes arranged on a solid phase in addition to only a small amount of sample and which allows the detection of the reaction of many probes with high sensitivity and great ability of sequence recognition.

DISCLOSURE OF INVENTION

An objective of this invention is to solve the above-mentioned problems and to provide a solid phase for the detection of a target nucleic acid for the purpose of detecting a wide variety of target nucleic acids in a sample simultaneously with more ease, greater rapidity, and high accuracy or for the detection of a large number of base sequence groups contained in a target nucleic acid simultaneously with high accuracy, a preparation method thereof, and a method of detecting a target nucleic acid.

As a result of thorough investigations, the present inventors have found: a solid phase for the detection of a target nucleic acid which enables the detection of a wide variety of target nucleic acids in a sample simultaneously with more ease, greater rapidity, and high sensitivity; a preparation method thereof; and a method of detecting a target nucleic acid using said solid phase.

Specifically, this invention provides a solid phase for the detection of a target nucleic acid comprising a pair of probes, said pair of probes having a base sequence capable of sequentially hybridizing with a specified polynucleotide sequence of said target nucleic acid and being immobilized on said solid phase through a linker portion in such a manner as to occupy a restricted spatial arrangement so that the probes can be ligated by an enzyme when the probes sequentially hybridize with the specified polynucleotide sequence of said target nucleic acid.

Also, the invention provides the solid phase for the detection of a target nucleic acid as described above, characterized being produced by the step wherein the pair of probes immobilized through the linker portion in such a manner as to occupy a restricted spatial arrangement hybridizes with said target nucleic acid to form a complex.

Also, the invention provides the solid phase for the detection of a target nucleic acid as described above, wherein at least one of the pair of probes is further provided with a base sequence capable of hybridizing with a padlock probe.

Further, the invention provides a method of preparing a solid phase for the detection of a target nucleic acid, said method comprising the steps of:

(1) hybridizing a pair of probes with the target nucleic acid to form a complex, said pair of probes having a base sequence capable of sequentially hybridizing with a specified polynucleotide sequence of the target nucleic acid;

(2) immobilizing the pair of probes having formed the complex, on a surface of the solid phase through a linker portion; and (3) denaturing and removing the target nucleic acid.

Also, the invention provides the method of preparation as described above, wherein the linker portion is formed by a binding reaction of biotin with avidin or streptavidin.

Also, the invention provides the method of preparation as described above, wherein at least one of the pair of probes is further provided with a base sequence capable of hybridizing with a padlock probe.

Further, the invention provides a solid phase for detection, characterized by being produced by the method of preparation as described above.

Still further, the invention provides a method of detecting a target nucleic acid comprising the steps of:

(1) hybridizing a solid phase for the detection of a target nucleic acid with the target nucleic acid to form a complex, said solid phase comprising a pair of probes, said pair of probes having a base sequence capable of sequentially hybridizing with a specified polynucleotide sequence of said target nucleic acid and being immobilized on said solid phase through a linker portion in such a manner as to occupy a restricted spatial arrangement so that the probes can be ligated by an enzyme when the probes sequentially hybridize with the specified polynucleotide sequence of said target nucleic acid;

(2) ligating the pair of probes by a ligase reaction of the complex to form a ligation product; and (3) detecting the ligation product.

Also, the invention provides the method of detection as described above, wherein the ligation product is detected based on a resistance activity thereof against exonuclease digestion in the step for detection of the ligation product.

Also, the invention provides the method of detection as described above, wherein the resistance activity of the ligation product against the exonuclease digestion is detected based on mass variations of the solid phase for the detection of a target nucleic acid.

Also, the invention provides the method of detection as described above, wherein the mass variations of the solid phase for the detection of a target nucleic acid is based on fluctuations of reflective index as determined by the surface plasmon resonance sensor.

In addition, the invention provides a method of detecting a target nucleic acid comprising the steps of:

(1) hybridizing a solid phase for the detection of a target nucleic acid with the target nucleic acid to form a complex, said solid phase comprising a pair of probes, said pair of probes having a base sequence capable of sequentially hybridizing with a specified polynucleotide sequence of said target nucleic acid and a base sequence capable of hybridizing with a padlock probe, and being immobilized on said solid phase through a linker portion in such a manner as to occupy a restricted spatial arrangement so that the probes can be ligated by an enzyme when the probes sequentially hybridize with the specified polynucleotide sequence of said target nucleic acid;

(2) ligating the pair of probes by a ligase reaction of the complex to form a ligation product;

(3) hybridizing the ligation product with the padlock probe;

(4) ring-closing the padlock probe to the ligation product in a continuous loop by a ligase reaction; and (5) detecting the ring-closed padlock probe.

BRIEF DESCRIPTION OF DRAWINGS

FIG. 8 illustrates an embodiment of the method of detecting a large number of sequences simultaneously with high accuracy, which utilizes the method according to this invention.

BEST MODE FOR CARRYING OUT THE INVENTION

The solid phases and methods for the detection of target nucleic acids according to this invention will be explained in detail hereinbelow.

Target Nucleic Acids

Figure 1:
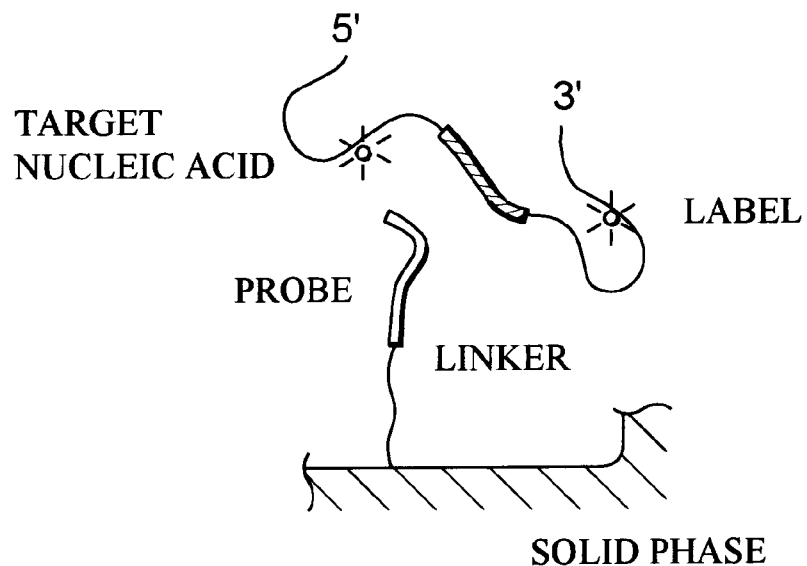
FIG. 1 illustrates a method to hybridize a specified polynucleotide sequence with a single probe immobilized on a solid phase and to detect the sequence.
Figure 1:
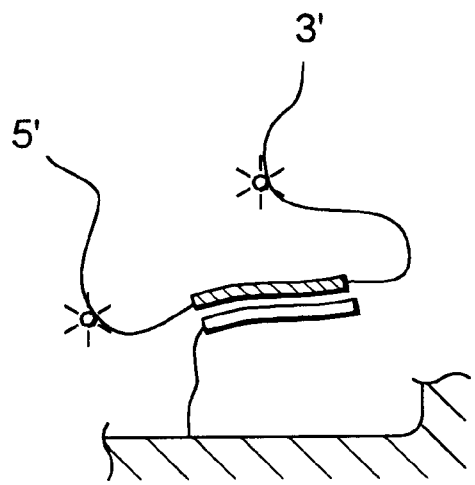
Figure 2:
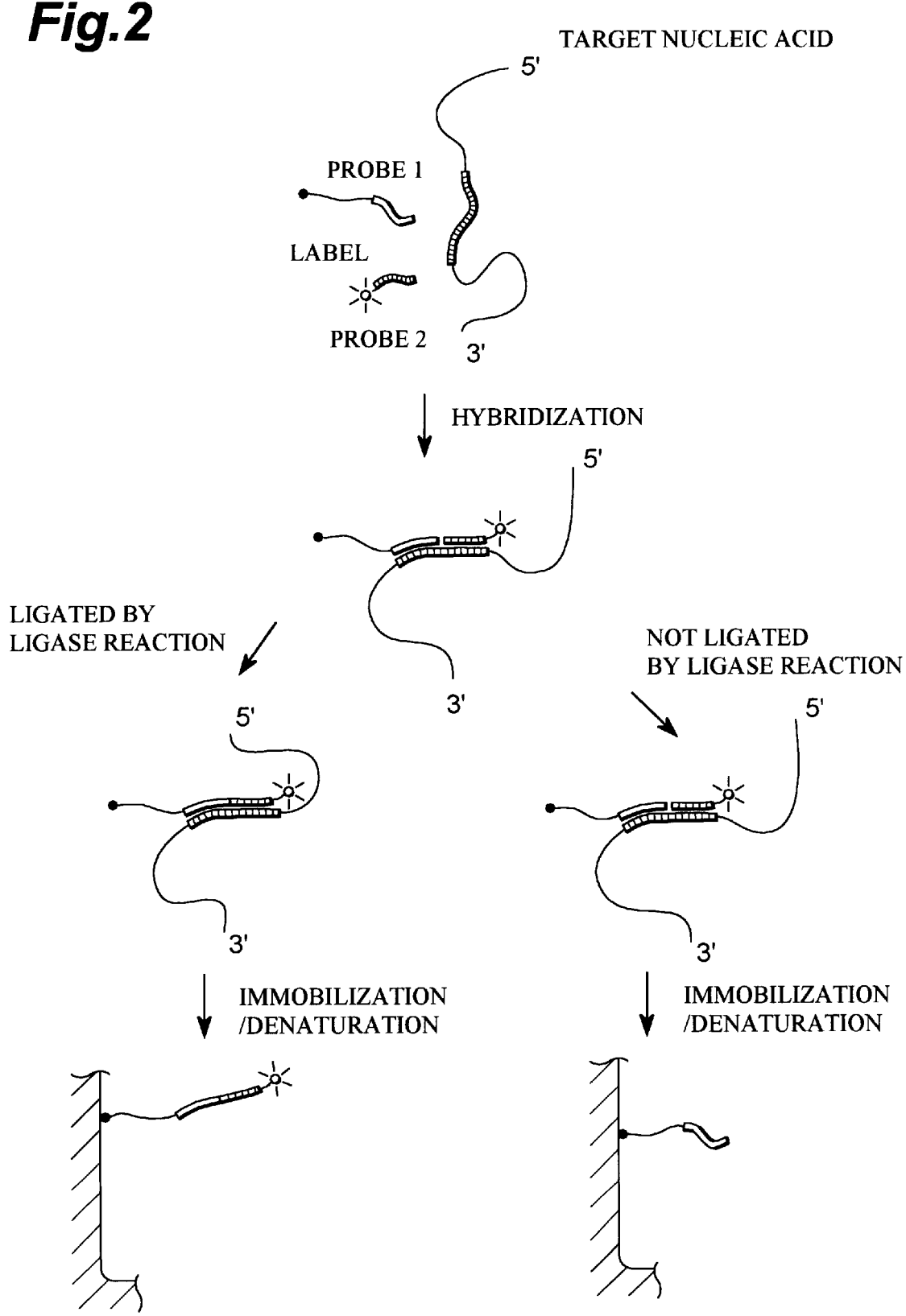
FIG. 2 illustrates a method where after two kinds of probes have been allowed to hybridize with a specified polynucleotide sequence, they are ligated by a ligase reaction and immobilized on a solid phase to achieve their detection.
Figure 3:
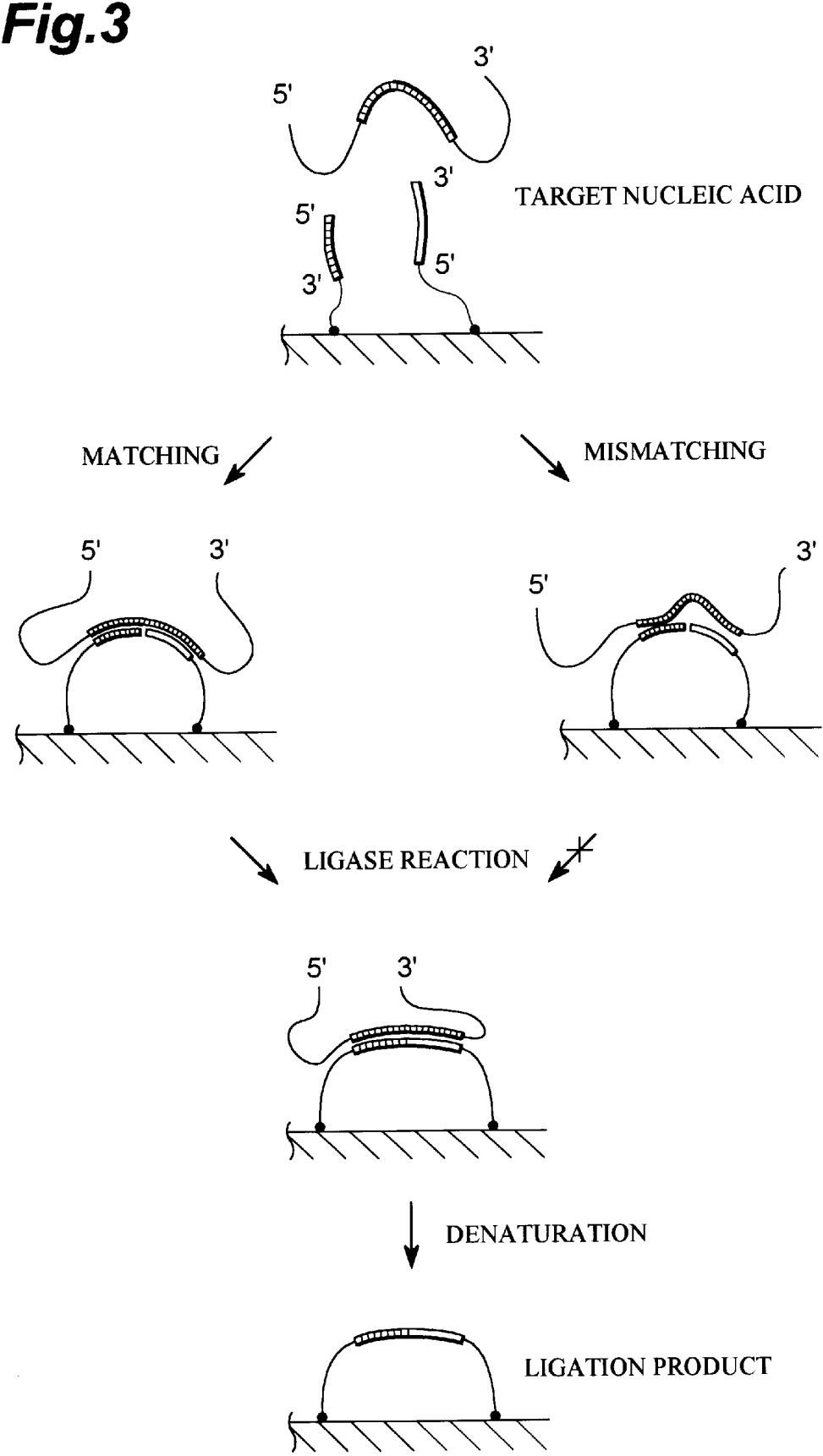
FIG. 3 illustrates a method to detect a target nucleic acid employing the solid phase for the detection of a target nucleic acid according to this invention.

In this invention the types of target nucleic acids are not particularly limited and a variety of nucleic acids (such as DNAs, RNAs, and oligonucleotides) are applicable. There is also no particular limitation concerning the length of the target nucleic acids and usable are nucleic acids the length of which has been adjusted to appropriate sizes by suitable treatments depending on intended purposes. As is schematically shown in FIG. 3, this invention relates to a method of detecting a specified polynucleotide in a target nucleic acid, which method uses two kinds of probes each having a base sequence capable of hybridizing with this specified oligonucleotide sequence. Therefore, this polynucleotide sequence needs to be previously known, but its base number should not be particularly limited. The specified polynucleotide sequences of the invention may be at least 20 bases in number to enable sufficient recognition and to be suited for the ligase reaction as will be described hereinbelow. More preferably, they may be more than 30 bases. As to the position of this specified sequence in the target nucleic acid, there is also no particular limitation; it may be in the vicinity of the end or at the middle portion of the nucleic acid.

Furthermore, when the methods according to this invention are practiced, the above-mentioned specified polynucleotide sequence portions at least need to be single-stranded in order to effect hybridization; however, in cases where the target nucleic acids are double-stranded, they can be easily made single-stranded by conventional means such as heat denaturation or alkaline denaturation.

A Pair of Probes

The pair of probes according to this invention has base sequences complementary to the above-mentioned specified polynucleotide sequence portion of the target nucleic acid and sequentially hybridizes with the above-mentioned specified polynucleotide sequence portion. There is no particular limitation to the base numbers of base sequence of the respective probes. In the invention, the base number may be more than about 10 and preferably more than 15. Where the base number is small, the sufficient specified recognition function is not observed and too many numbers bring out problems such as handling or preservation.

Moreover, each probe is provided with a linker portion for the purpose of its immobilization on the solid phase for detection, which will be explained hereinbelow.

The Solid Phase for Detection

In this invention "the solid phase" means a solid phase medium where the two kinds of probes as explained above are bound onto its surface in proximity with each other. Among others their binding densities are not particularly limited and those bound with different densities can be used. In addition, the types of the solid phase media are also not particularly limited and solid phase media of inorganic substances or solid phase media of organic substances can be used, for example. As the solid phase media of inorganic substances various metallic films, silica gel, alumina, glass, etc. are named. As the solid phase media of organic substances nitrocellulose films, nylon films, etc. are named. In this invention it is particularly preferred to use media made of metallic films bound with dextran.

Linker Portions

According to this invention, the solid phase for detection and the above-mentioned kinds of probes are bound together through a linker portion. The type and shape (or the like) of the linker portion are not particularly limited. The linker portions may suffice insofar as they posses enough strong binding ability in: the conditions where the above-mentioned two kinds of probes hybridize with the target nucleic acids; the accompanying washings; and other manipulations such as removing the target nucleic acids.

Specifically, named as linker portions are, for example, those utilizing ordinary chemical bonding, and those utilizing bonding based on interaction between proteins themselves or strong interaction between proteins and specified molecules. In the invention, the binding based on strong interaction between proteins and specified molecules are preferably utilized. More specifically, they are binding between biotin and avidin or between biotin and streptavidin. In these instances, although not particularly limited thereto, biotin is bound to the probes and avidin or streptavidin is bound to the solid phase, which makes a preferable combination.

Spatial Arrangement

According to this invention, the solid phase for detection is immobilized on a solid phase such that two kinds of probes occupy a predetermined spatial arrangement. Namely, it is the spatial arrangement that allows the above-mentioned probes to sequentially hybridize with the specified polynucleotide sequence of the target nucleic acid and then to be ligated by enzyme reactions.

The methods to immobilize the probes with the predetermined spatial arrangement as described above include a method wherein the above-mentioned two kinds of probes are premixed to provide their desirable concentrations and the mixture is allowed to react with the solid phase for detection to achieve their bonding through the linker portions, for example. In this case, there is obtained an arrangement where the two kinds of probes are randomly bound to the above-mentioned surface. Here, it is believed that among the spatial arrangements of the two kinds of probes as described above, only a very small number of the probes take that which allows the sequential hybridization with the specified polynucleotide sequence of the target nucleic acid and further the ligation by enzyme reactions.

Figure 4:
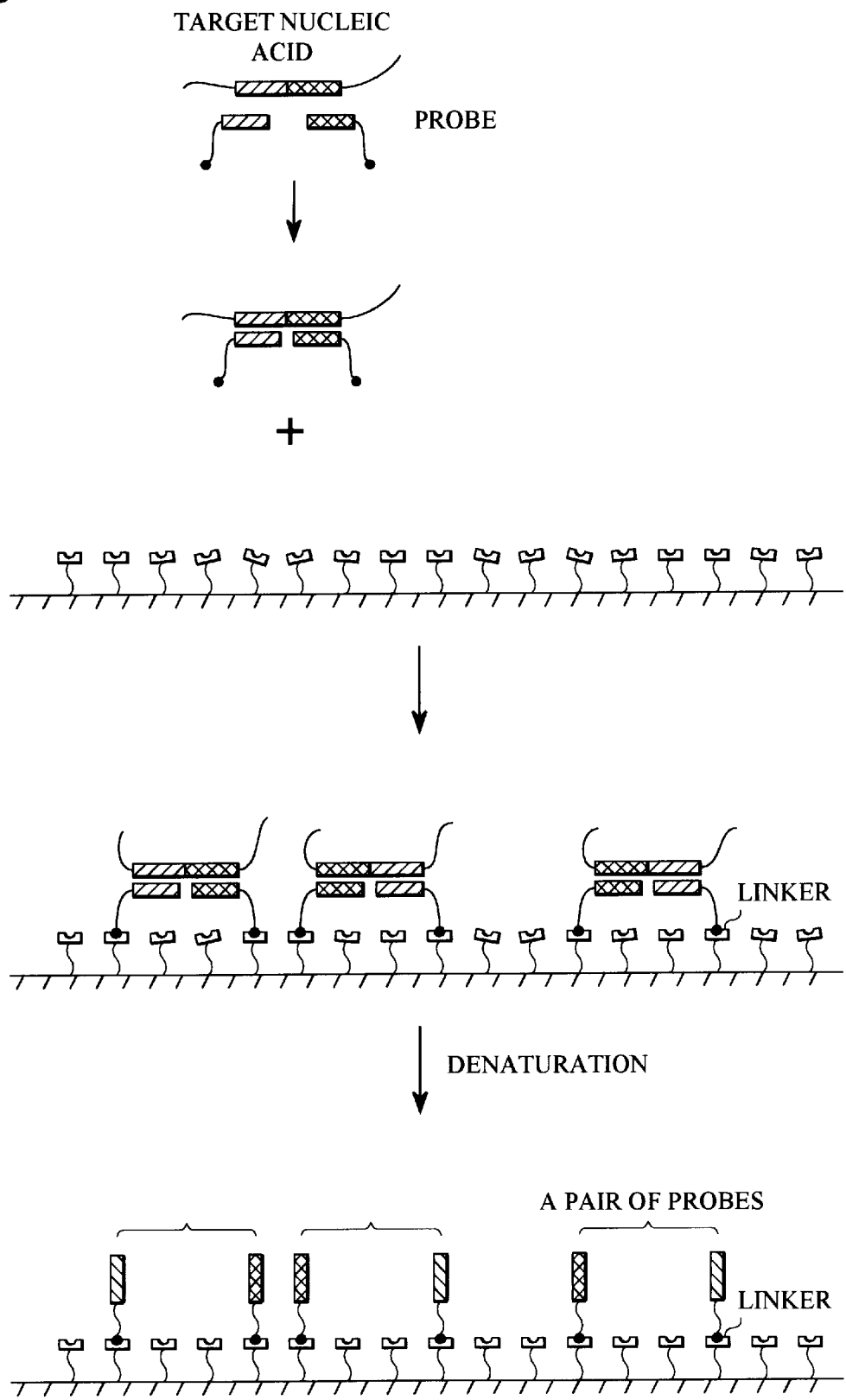
FIG. 4 illustrates an example of the preparation methods of the solid phase for the detection of a target nucleic acid according to the invention.

According to this invention, the techniques as described below can preferably be used as a method to immobilize as many pairs of probes as possible on the solid phase, which probes have desirable spatial arrangements (see FIG. 4).

The two kinds of probes are first mixed with the target nucleic acid to effect hybridization. The resulting hybrids are allowed to cause binding reaction on the solid phase for detection, which immobilizes the hybrids thereon. After thoroughly washing the above-mentioned solid phase, the target nucleic acids are removed from the hybrids by heat treatment, alkaline treatment or the like.

Following the manipulations as described above, the two kinds of probes have come to being immobilized on the solid phase in such a desirable spatial arrangement as to hybridize with the target nucleic acid.

In addition, the target nucleic acid to be used in this case does not necessarily have a continuous sequence that is completely complementary to the polynucleotide sequence portions of the two kinds of probes as described above and it is only required that the target nucleic acid be able to hybridize the ends of the two kinds of probes in proximity with each other.

Hybridization Conditions

In this invention, there is no particular limitation to the conditions of hybridization between the pair of probes and the target nucleic acid in accordance with the invention and standard conditions are usable. For example, the method as described in "Molecular Biology Experimental Manual"; M. Kawakami Ed.; Kodansha, pp. 172 or its modification may be used. Also, there is no particular limitation to the conditions under which the target nucleic acids are removed from the resulting hybrids to form single-strands and standard conditions known in the art are usable. For example, they are alkaline treatment, heat treatment, acid treatment and the like.

Enzymes

According to this invention, the enzymes which can be used to bind a pair of two kinds of probes include a ligase, for example. The type and reaction conditions of ligases are not particularly limited and a variety of ligase reactions known in the art are usable in accordance with standard selections.

Further, after ligation resulting from the ligase reaction, it is possible to remove the target nucleic acids following various manipulations (such as heat treatment, alkaline treatment, and acid treatment).

Methods of Detection

As shown in FIG. 3, the method of detecting a target nucleic acid according to this invention utilizes the solid phase for detection of the invention; allows a pair of probes on the aforementioned solid phase for detection to sequentially hybridize with a specified polynucleotide sequence of the target nucleic acid; causes bonding between the two kinds of probes as described above to take place through the ligase reaction of the resultant hybrids (complexes); and detects the ligation products obtained therefrom.

Also, in cases where the base sequence of the target nucleic acid differs and the probes erroneously recognize the sequence, the formation of the above-mentioned ligation product does not result from the ligase reaction. Thus when the target nucleic acid is removed by alkaline treatment or the like after the ligase reaction as described above, the probes have not been ligated together and the respective ends remain to exist. In other words, the pair of probes returns to its initial state.

According to this invention, it is possible to find out that the above-mentioned ligase reaction has occurred and therefore, to find out the presence of the target nucleic acid by detecting the ligation products as described above through various means. In this case, since the ligase reaction has extremely high specificity, the degree of erroneous recognition can be kept to a very low level.

Concerning the means to detect the above-mentioned ligation product in accordance with the invention, a variety of methods known in the art can be used as will be described below.

Figure 5:
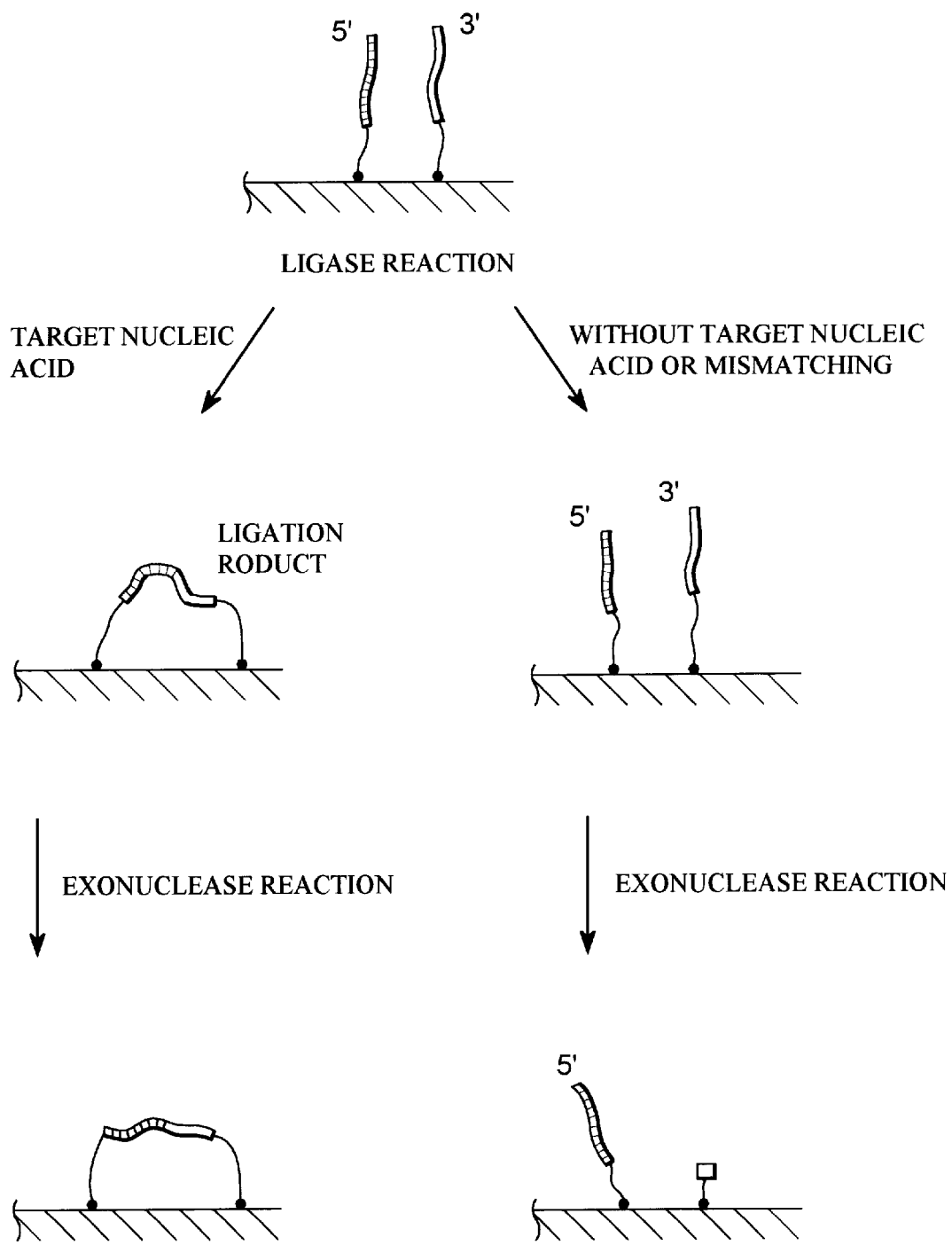
FIG. 5 illustrates a method of detecting a ligation product, wherein a probe having formed a complex does not react with Exonuclease I and a probe having formed no complex either in the absence of a specified polynucleotide or due to mismatching is digested with Exonuclease I.

For example, an exonuclease reaction (such as Exonuclease I, VII) may be utilized as shown in FIG. 5. On the one hand, where the above-mentioned ligation product is not formed, the pair of probes on the solid phase is in its initial state with the 5'- and 3'-ends being present. Thus when Exonuclease I reaction is performed here, for example, one probe is digested (or hydrolyzed) from its 3'-end. On the other hand, because no 3'-end exists in the ligation product, the probes are not digested even if the exonuclease reaction is performed here. Therefore, it is possible to detect the presence of the above-mentioned structure in a closed-ring form by detecting the presence of hydrolyzed products or hydrolyzed probes. To this end, the digestion of the probes can be ascertained by labeling the probes with various labels (such as fluorescence or radioisotope) or by detecting decreases in the mass of the nucleic acids on the solid phase, e.g., by surface plasmon resonance.

Figure 6:
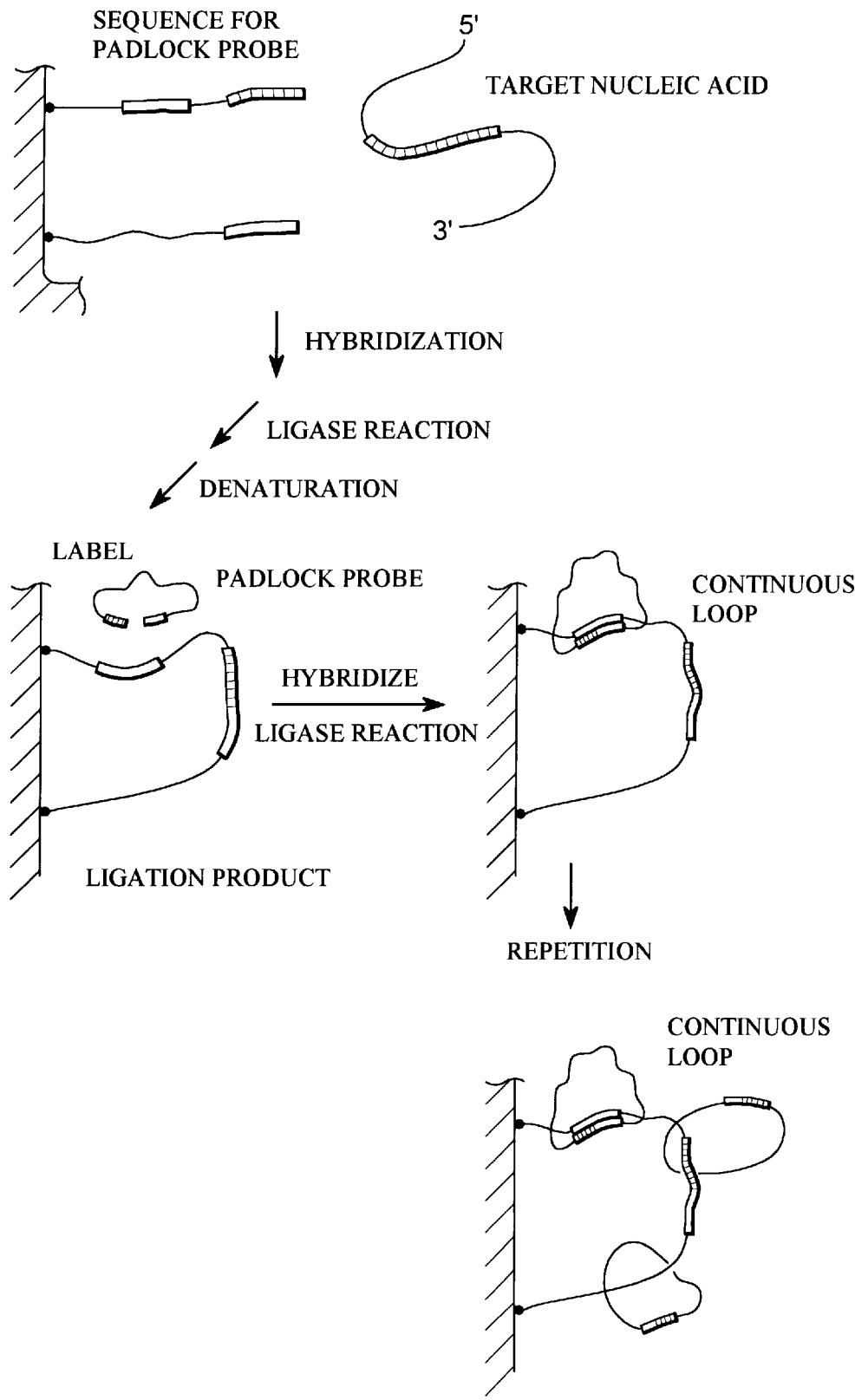
FIG. 6. illustrates a method wherein a probe having an oligonucleotide sequence for a padlock probe is used to hybridize with a specified polynucleotide sequence and to obtain a ligation product by a ligase reaction, and the padlock probe is allowed to hybridize with the resultant ligation product and is subjected to the ligase reaction, causing a continuous loop to be formed.

Also, as is shown in FIG. 6, one of the detection methods as described above is a method where the above-mentioned ligation product is allowed to hybridize with a padlock probe, the padlock probe is then ring-closed with the ligation product in a continuous loop through a ligase reaction, and the ring-closed padlock probe is detected. If necessary, it is possible to amplify the reaction by further repeating these manipulations and adding plural padlock probes. Labeling of the padlock probes is made with fluorescent molecules or radioisotopes or the like. The term "padlock probe" herein means a probe connecting two segments through a linker sequence which segments hybridize with a sequence to be tested, the probe being an oligonucleotide probe cyclizing with both ends in proximity with each other when it has hybridized with the sequence to be tested (Science (1994), 265, 2085–2088).

Figure 7:
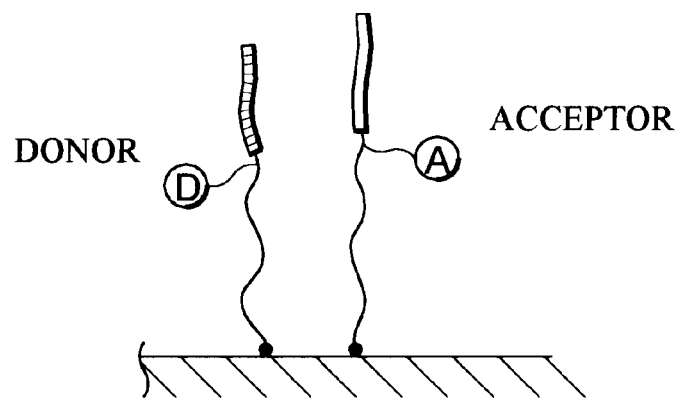
FIG. 7 illustrates a method wherein after probes are labeled with an energy donor and energy acceptor, respectively, allowed to hybridize with a specified polynucleotide sequence and subjected to a ligase reaction, the resultant ligation product is detected based on an energy donor-acceptor interaction between the labels.
Figure 7:
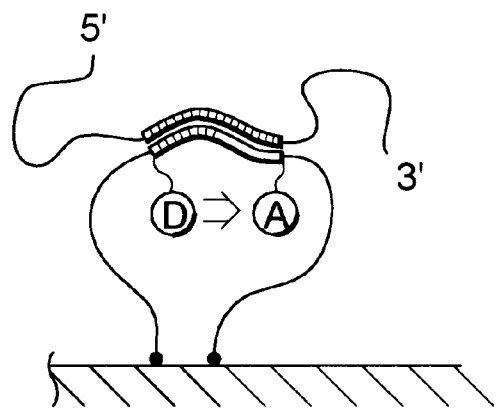

Furthermore, as is shown in FIG. 7, the technique for detecting the above-mentioned ligation product labels the two probes as described above respectively in advance and retains the labeling groups at specified positions by virtue of formation of the above-mentioned ligation product, thus causing specific interaction: by detecting the interaction, it is possible to find the presence of the above-mentioned ligation product. Labeling which can preferably be used in this case is, for example, based on the phenomenon of fluorescence energy transfer between molecules. In one instance, where probes labeled with fluorescent molecules of the energy donor type and those labeled with fluorescent molecules of the energy acceptor type are used, the fluorescent molecules of the energy donor which have been photoexcited resulting from the fluorescence energy transfer excite adjacent fluorescent molecules of the energy acceptor type and thus the fluorescent molecules of the energy acceptor type emit fluorescence when the probes are ligated. Observation of that fluorescence enables the detection of the ligation product.

Simultaneous, High Accuracy Detection of Multiple Sequence Target Nucleic Acids According to the methods of this invention, it becomes possible to simultaneously and individually detect many kinds of target nucleic acids in a sample to be tested (e.g., a mixture of one DNA and others or a wide variety of DNAs). For example, (a) the probes according to the invention as explained above are provided on the solid phase such as a filter; they are positioned so as to be able to efficiently hybridize with specified polynucleotide sequences in the respective target nucleic acids. (b) A mixture of the target nucleic acids in the sample is allowed to react at one time and further, a ligase reaction is performed at once. Through these manipulations the probes hybridize (and by the ligase reaction) with the specified sequences of the target nucleic acids correspondingly to form ligation products. (c) It is possible to simultaneously detect the presence of the sequences of many kinds of the target nucleic acids by detecting those ligation products according to various methods as explained above.

For instance, FIG. 8 shows an embodiment of practicing the method for the simultaneous, high accuracy detection of multiple sequence target nucleic acids. First, where the specified polynucleotide sequences of the target nucleic acids to be detected are five kinds, namely No. 1 through No. 5, pairs of probes corresponding to the specified polynucleotide sequences Nos. 1–5 are provided at respective predetermined sites. In this case, their preparations are preferably made following the method illustrated in FIG. 4 as described to explain the invention. At all sites the target nucleic acids are allowed to cause hybridization and an excess amount of samples is washed and removed. Then the binding reaction by means of ligase is conducted at all the sites, when ligation products are formed only in the cases where the corresponding, specified polynucleotide sequences are present. In FIG. 8 Nos. 1, 3 and 5 are the cases. As to the method to detect the resulting ligation products which will follow, a variety of methods already explained so far can be used. The sites at which the presence of ligation products is confirmed permit the detection of plural target nucleic acids existing in the sample being tested.

Although this invention will be hereinbelow concretely illustrated by examples, it is not limited to the following examples insofar as it does not depart from its essence. Nucleic acids were generally synthesized on a automated oligonucleotide synthesizer by following the solid phase phosphoramidite synthetic method and purified by ion-exchange high performance liquid chromatography (purity greater than 99%). The 5'-phosphorylation was carried out using 5' Phosphate-ON. The 3'-biotinylation was carried out using 3'-Biotin-ON CPG. The 5'-biotinylation was carried out using Biotin-ON Phosphramidite. The foregoing reagents are available from CLONTECH Inc.

EXAMPLE 1

Immobilization of Probes (1-1) Probe A (5' (P)-TAGTGGATCCCCCGGGCTGC-(biotin) 3') (SEQ ID NO: 1) comprising a 20 base oligonucleotide the 3'-end of which was labeled with biotin and the 5'-end of which was phosphorylated was synthesized by the conventional phosphoramidite solid phase synthetic method using automated oligonucleotide synthesizer.

(1-2) Probe B (5' (biotin)-GGTGGCGGCCGCTCTAGAAC-3') comprising a 20 base oligonucleotide the 5'-end of which was labeled with biotin was synthesized by the conventional phosphoramidite solid phase synthetic method using automated oligonucleotide synthesizer.

(1-3) Target nucleic acid A comprising an oligonucleotide with the following sequence was synthesized to serve as a target nucleic acid capable of retaining the above-mentioned two probes in proximity to each other:
5'-GCAGCCCGGGGGATCCACTAGTTCTAGAGCGGCC GCCACC-3'

(1-4) The probes obtained in Steps (1-1) and (1-2) (each 400 nM) and the target nucleic acid (400 nM) obtained in Step (1-3) were mixed in 1×SSPE (which contained 150 mM NaCl, 10 mM sodium dihydrogenphosphate, and 1 mM ethylenediaminetetraacetic acid with the pH adjusted to 7.4 with sodium hydroxide), the mixed solution was heated in boiling water for 3 min to effect denaturation and then maintained at 55° C. for 10 min to effect hybridization.

(1-5) When the complex prepared in Step (1-4) was reacted with a BIAcore sensor chip SA5 (Pharmacia Biotech Inc.) coated with streptavidin at 37° C. for 4 min, mass variations of the solid phase were observed with a surface plasmon resonance sensor (BIAcore 2000 available from Pharmacia Biotech). An increase of 1035~1460 resonance units (which represent values indicating attenuation angles of reflected light in the surface plasmon resonance and which reflect the mass variations of a solid surface) was noted, and this suggested that the complex was bound on the sensor chip through its biotin-streptavidin binding.

(1-6) When the solid phase bound to the complex as prepared in Step (1-5) was reacted with a solution of 10 mM sodium hydroxide at 37° C. for 1 min, its mass variations were observed with the surface plasmon resonance sensor. An increase of 622~859 resonance units was noted, and this suggests that the sequence having retained two probes in proximity with each other was dissociated by alkaline denaturation.

(1-7) When the solid phase as described in Step (1-6) where the sequence having retained two probes in proximity with each other had been dissociated was again reacted with the same target nucleic acid A (2250 nM) in 1×SSPE at 37° C. for 4 min, its mass variations were observed with the surface plasmon resonance sensor. An increase of 656~704 resonance units was noted, and it ascertained that the solid phase prepared in Step (1-6) hybridized to the sequence of the target nucleic acid. Also, the amount of this binding is nearly equal to that of the target nucleic acid which was used to retain the two probes in proximity with each other and was removed. This result suggests that the solid phase prepared in Step (1-6) efficiently binds to the target nucleic acid.

EXAMPLE 2

Ligase Ligation on a Solid Phase
Solid Phase Ligation of Probes Hybridized in a Liquid Phase to Specified Sequences of the Target Nucleic Acid (2-1) The probes obtained in Steps (1-1) and (1-2) of Example 1 (each 400 nM) and the sequence (400 nM) obtained in Step (1-3) and capable of retaining the two probes in proximity with each other were mixed in 1×SSPE, heated in boiling water for 3 min to effect denaturation, and then maintained at 55° C. for 10 min to effect hybridization.

(2-2) The complex between the probes and the sequence capable of retaining the two probes in proximity with each other as prepared in Step (2-1) was reacted with the BIAcore sensor chip SA5 coated with streptavidin at 37° C. for 4 min, achieving its binding through the biotin-streptavidin binding.

(2-3) After the solid phase bound to the complex as prepared in Step (2-2) was reacted with T4DNA ligase (T4 DNA Ligase, 3500 IU/ml available from TAKARA SHUZO Co. Ltd.) diluted with a reaction buffer as attached at 37° C. for 20 min, it was twice (each at 37° C. for 1 min) washed with 0.1% SDS (sodium dodecyl sulfate) to remove the enzyme, and further reacted with a solution of 10 mM sodium hydroxide at 37° C. for 1 min, whereby the sequence having retained two probes in proximity with each other was dissociated.

(2-4) After the solid phase subjected to the manipulation as described in (2-3) was reacted with Exonuclease I (2500 unit/ml; available from Amersham Inc.) diluted with a 67 mM glycine-sodium hydroxide buffer (pH 9.5) containing 10 mM 2-mercaptoethanol and 6.7 mM magnesium chloride at 37° C. for 20 min, it was twice (each at 37° C. for 1 min) washed with 0.1% SDS to remove the enzyme. Mass variations of the solid phase in this manipulation were observed with the surface plasmon resonance sensor. Although the decrease remained as small as 93~103 resonance units, a decrease of 173~213 resonance units in the solid phase mass was noted in the case where the solid phase was not subjected to the action of a ligase as in Step (2-3). These results suggest that the two probes retained in proximity with each other by the target sequence have gained resistance to the exonuclease digestion by being bound on the solid phase through the ligase.

EXAMPLE 3

Ligase Ligation on the Solid Phase
Solid Phase Ligation of Probes Hybridized on a Solid Phase to Specified Sequences of the Target Nucleic Acid Employing the solid phase prepared in Step (1-7) on which the probes and the specified sequences of the target nucleic acid were bound again, the ligation with ligase as described in Step (2-3) of Example 2 was carried out and thereafter, the target nucleic acid was dissociated by reaction with a 10 mM sodium hydroxide solution at 37° C. for 1 min. Mass variations of the solid phase by digestion with an exonuclease as described in Step (2-4) were observed with the surface plasmon resonance sensor. Although the decrease remained as small as 65 units, a decrease of as large as 163 resonance units in the solid phase mass was noted in the case where the solid phase was not subjected to the action of ligase. These results suggest that when the two probes bound to an immobilization medium are allowed to hybridize with the target nucleic acid, they can be ligated with a ligase by being in proximity with each other.

COMPARATIVE EXAMPLE 1

After Probe A (340 nM) diluted with a TE buffer (10 mM Tris-HCl buffer containing 1 mM ethylenediaminetetraacetic acid; pH 8.0) was heated in boiling water for 3 min, it was immediately ice-cooled to provide a sample. The sample was observed under a BIAcore sensor chip SA5 coated with streptavidin at 37° C. for 4 min and an increase of 90 resonance units was noted. Specifically, this suggests that Probe A, which is single-stranded, can scarcely bind to the solid phase by itself.

COMPARATIVE EXAMPLE 2

After Probe B (775 nM) diluted with a TE buffer was heated in boiling water for 3 min, it was immediately ice-cooled to provide a sample. The sample was observed under the BIAcore sensor chip SA5 coated with streptavidin at 37° C. for 4 min and an increase of 91 resonance units was noted. Specifically, this suggests that Probe B, which is single-stranded, can scarcely bind to the solid phase by itself.

COMPARATIVE EXAMPLE 3

Probe C (5'(P)-TAGTGGATCCCCCGGGCTGCAGGAATTCGATATCAAGCTT-(biotin) 3'; 25 μM) and probe D (5' (biotin)-GCGAATTGGAGCTCCACCGCGGTGGCGGCCGCTCTAGAAC-3'; 25 μM), both of which were diluted with a TE buffer, were mixed in equal volumes, heated in boiling water for 3 min and thereafter, immediately ice-cooled to provide a sample. The sample was observed under the BIAcore sensor chip SA5 coated with streptavidin at 37° C. for 1~4 min, when an increase of 84~99 resonance units was noted.

Specifically, this suggests that the two probes, Probes C and D, upon mere mixing do not sufficiently bind to the solid phase.

EXAMPLE 4

Probe C (170 nM) and Probe D (180 nM), both diluted with a TE buffer, and a sequence for probe ligation diluted with 1×SSPE (5'-GCAGCCCGGG GGATCCACTAAGTTCTAGAGCGGCCGCCACC-3': this sequence is the one that is obtained by insertion of "A" into the sequence of the target nucleic acid at its middle part (used in Example 1) and is able to position the two probes being aligned, but it contains a mismatch; 1.2 μM) were mixed in a volume ratio of 2:2:1, heated in boiling water for 3 min to effect denaturation, and thereafter, were maintained at 55° C. for 10 min to provide a hybridized sample. When the sample was reacted with the BIAcore sensor chip SA5 coated with streptavidin at 370C for 4 min, mass variations of the solid phase were observed with the surface plasmon resonance sensor. An increase of 330 resonance units was noted.

This suggests that where Probes C and D have been allowed to prehybridize with the sequence for probe ligation, an improvement in the amount of immobilization is recognized.

EXAMPLE 5

Probe A (340 nM) and Probe B (775 nM), both diluted with a TE buffer, and the sequence for probe ligation (1.2 μM) diluted with 1×SSPE were mixed in a volume ratio of 2:2:1, heated in boiling water for 3 min to effect denaturation and thereafter, were maintained at 55° C. for 10 min to provide a hybridized sample. When the sample was reacted with the BIAcore sensor chip SA5 coated with streptavidin at 37° C. for 4 min, mass variations of the solid phase were observed with the surface plasmon resonance sensor. An increase of 1173 resonance units was noted.

This suggests that where Probes A and B have been allowed to prehybridize with the sequence for probe ligation, an improvement in the amount of immobilization is recognized.

EXAMPLE 6

Probes A and B (each 400 nM), and the target nucleic acid A (400 nM) capable of retaining these probes in proximity with each other were mixed in 1×SSPE, the mixed solution was heated at 100° C. for 5 min to effect denaturation and thereafter, maintained at 55° C. for 10 min to effect hybridization, forming a complex.

The above-mentioned complex was diluted 10-fold with 1×SSPE and reacted with the BIAcore sensor chip SA5 coated with streptavidin at 37° C. for 5 min, achieving its binding through the biotin-streptavidin binding. Thereafter, it was successively washed with 0.1% SDS, 10 mM sodium hydroxide, and 10 mM hydrochloric acid each at 37° C. for 1 min to remove the target nucleic acid A and to form a solid phase for the detection of any target nucleic acid.

When the above-mentioned solid phase for the detection of a target nucleic acid was reacted with samples which had been diluted with 1×SSPE to provide 400 nM of respective sequences as described below, their mass variations were observed with the surface plasmon resonance sensor. Increases of 407~769 resonance units were noted. This suggests that since any of the sequences binds to the solid phase, the nucleic acid sequence to be detected can not be distinguished from nucleic acids differing to slight degrees in terms of the binding amounts based on hybridization.

The sequences which were used as samples are as follows:

```
Target Nucleic Acid A;
5'-GCAGCCCGGG GGATCCACTA GTTCTAGAGC GGCCGCCACC-3'

Sequence A devoid of one base;
5'-GCAGCCCGGG GGATCCACT GTTCTAGAGC GGCCGCCACC-3'

Sequence B devoid of one base;
5'-GCAGCCCGGG GGATCCACTA TTCTAGAGC GGCCGCCACC-3'

Sequence with one extra base;
5'-GCAGCCCGGG GGATCCACTAAGTTCTAGAGC GGCCGCCACC-3'

Sequence A substituted in one base;
5'-GCAGCCCGGG GGATCCACTT GTTCTAGAGC GGCCGCCACC-3'

Sequence B substituted in one base;
5'-GCAGCCCGGG GGATCCACTG GTTCTAGAGC GGCCGCCACC-3'

Sequence C substituted in one base;
5'-GCAGCCCGGG GGATCCACTC GTTCTAGAGC GGCCGCCACC-3'

Sequence D substituted in one base;
5'-GCAGCCCGGG GGATCCACTA ATTCTAGAGC GGCCGCCACC-3'

Sequence E substituted in one base;
5'-GCAGCCCGGG GGATCCACTA TTTCTAGAGC GGCCGCCACC-3'

Sequence F substituted in one base;
5'-GCAGCCCGGG GGATCCACTA CTTCTAGAGC GGCCGCCACC-3'
```

This solid phase was reacted with T4 DNA ligase (3500 IU/ml) diluted with a reaction buffer as attached at 37° C. for 5 min and successively washed with 0.1% SDS, 10 mM sodium hydroxide, and 10 mM hydrochloric acid each at 37° C. for 1 min to remove the ligase and the samples as well.

This solid phase was reacted with Exonuclease I (1000 unit/ml) diluted with a 67 mM glycine-sodium hydroxide buffer (pH 9.5) containing 10 mM 2-mercaptoethanol and 6.7 mM magnesium chloride at 37° C. for 20 min and it was further washed with a TE buffer for 30 min, when mass variations of the solid phase were observed with the surface plasmon resonance sensor. Although the decrease remained as small as 50~54 resonance units when the nucleic acid A was reacted, decreases of 123 and 131 resonance units were noted for the sequence A devoid of one base and a decrease of as large as 125 resonance units was noted for the sequence with one extra base. Further, also in the case of the sequence with substitution of one base, the mass decrease of the solid phase on the order of 64~135 resonance units was noted, although there were differences depending upon the type of substitution, which was greater than those obtained when the target nucleic acid was reacted.

This suggests that the method of this invention can recognize such a slight difference in sequence as will not be distinguished by the binding amounts based on hybridization.

| Sequences to be tested | Solid phase mass variations (RU) | | |
|---|---|---|---|
| | Immobilization step | Hybridization step | Digestion step |
| Target nucleic acid A | 654 | 596 | −54 |
| Target nucleic acid A | 571 | 527 | −50 |
| Target nucleic acid A | 452 | 451 | −51 |
| Sequence with one extra base | 578 | 407 | −125 |
| Sequence A devoid of one base | 571 | 509 | −123 |
| Sequence B devoid of one base | 604 | 502 | −131 |
| Sequence A substituted in one base | 569 | 404 | −68 |
| Sequence B substituted in one base | 565 | 520 | −119 |
| Sequence C substituted in one base | 612 | 769 | −96 |
| Sequence D substituted in one base | 524 | 493 | −64 |
| Sequence E substituted in one base | 559 | 460 | −85 |
| Sequence F substituted in one base | 575 | 518 | −135 |

EXAMPLE 7

Probes A and D (each 400 nM), and the target nucleic acid B (5'-GCAGCCCGGG GGATCCACTAGTTCTAGAGCG-GCCGCCACCGCGGT GGAGCTCCAATTCGC-3'; 400 nM) capable of retaining these probes in proximity with each other were mixed in 1×SSPE, the mixed solution was heated at 100° C. for 5 min to effect denaturation and thereafter, maintained at 55° C. for 10 min to effect hybridization, forming a complex.

The above-mentioned complex was diluted 10-fold with 1×SSPE and reacted with the BIAcore sensor chip SA coated with streptavidin (available from Pharmacia Biotech Inc.) at 37° C. for 5 min, achieving its binding through the biotin-streptavidin binding. Thereafter, it was successively washed with 0.1% SDS, 10 mM sodium hydroxide, and 10 mM hydrochloric acid each at 37° C. for 1 min to remove the target nucleic acid B and to form a solid phase for the detection of any target nucleic acid.

When the above-mentioned solid phase for the detection of a target nucleic acid was reacted with samples at 37° C. for 10 min which had been diluted with 1×SSPE to provide 400 nM of respective sequences as described below, their mass variations were observed with the surface plasmon resonance sensor. Increases of 352~373 resonance units were noted. This suggests that since any of the sequences binds to the solid phase, the nucleic acid sequence to be detected can not be distinguished from nucleic acids differing to slight degrees in terms of the binding amounts based on hybridization. The sequences that were used as samples are as follows:

```
Target Nucleic Acid A;
5'-GCAGCCCGGG GGATCCACTA GTTCTAGAGC GGCCGCCACC-3'

Sequence A devoid of one base;
5'-GCAGCCCGGG GGATCCACTG TTCTAGAGCG GCCGCCACC-3'

Sequence with one extra base;
5'-GCAGCCCGGG GGATCCACTAA GTTCTAGAGC GGCCGCCACC-3'
```

This solid phase was reacted with T4 DNA ligase (3500 IU/ml) diluted with a reaction buffer as attached at 37° C. for 5 min and successively washed with 0.1% SDS, 10 mM sodium hydroxide, and 10 mM hydrochloric acid each at 37° C. for 1 min to remove the ligase and the samples as well.

When this solid phase was reacted with a padlock probe (5'-GCGGTGGAGC TCCAATTCGC TTTTTTTTTTTTTTTTTTTTTTTTTTTTTTTTTTTTTTTT TTTTTTTTTTGTTCTAGAGCGGCCGCCACC-3'), which was diluted with 1×SSPE to provide a concentration of 400 nM, at 37° C. for 10 min, mass variations of the solid phase were observed with the surface plasmon resonance sensor. An increase of 192~235 resonance units was noted. This suggests that the padlock probe has bound to Probe D.

After this solid phase was reacted with T4 DNA ligase (3500 IU/ml) diluted with a reaction buffer as attached at 37° C. for 5 min to ligate the padlock probe and cyclized, it was successively washed with 0.1% SDS, 10 mM sodium hydroxide, and 10 mM hydrochloric acid each at 37° C. for 1 min to remove the ligase as well as to dissociate the padlock probe. At this point, mass variations of the solid phase were observed with the surface plasmon resonance sensor. Although the decrease remained as small as 80 units in the case where the target nucleic acid A was reacted, a decrease of as large as 143 resonance units was noted for Sequence A devoid of one base, 130 resonance units for the sequence with one extra base noted, and further 132 resonance units noted in the case where absolutely no target nucleic acid was allowed to act upon the solid phase.

This suggests that the detection method using the padlock probe can also recognize such a slight difference in sequence as will not be distinguished by the binding amounts based on hybridization.

| Types of target sequences | Solid phase mass variations (RU) | | | |
| --- | --- | --- | --- | --- |
| | Immobilization step | Hybridization step | binding with padlock | Dissociation of padlock |
| Target nucleic acid A | 524 | 365 | 192 | −80 |
| No target nucleic acid | 531 | −9 | 234 | −132 |
| Sequence A Devoid of one base | 561 | 352 | 235 | −143 |
| Sequence with One extra base | 518 | 373 | 221 | −130 |

EXAMPLE 8

Method of Forming No Complex

Probes A and B (each 400 nM) were mixed in 1×SSPE, the mixed solution was heated at 100° C. for 5 min to effect denaturation and thereafter, it was immediately ice-cooled.

The above-mentioned probes were diluted 50-fold with 1×SSPE and reacted with the BIAcore sensor chip SA coated with streptavidin at 37° C. for 5 min, achieving their binding through the biotin-streptavidin binding. Thereafter, the solid phase was successively washed with 0.1% SDS, 10 mM sodium hydroxide, and 10 mM hydrochloric acid each at 37° C. for 1 min to remove the target nucleic acid A and to form a solid phase for the detection of any target nucleic acid.

When the above-mentioned solid phase for the detection of a target nucleic acid was reacted with samples at 37° C. for 10 min which had been diluted with 1×SSPE to provide 400 nM of respective sequences as described below, their mass variations were observed with the surface plasmon resonance sensor. Increases of 597~624 resonance units were noted.

The sequences that were used as samples are as follows:

```
Target Nucleic Acid A;
5'-GCAGCCCGGG GGATCCACTA GTTCTAGAGC GGCCGCCACC-3'

Sequence A devoid of one base;
5'-GCAGCCCGGG GGATCCACT GTTCTAGAGC GGCCGCCACC-3'

Sequence with one extra base;
5'-GCAGCCCGGG GGATCCACTAAG TTCTAGAGC GGCCGCCACC-3'
```

This solid phase was reacted with T4 DNA ligase (3500 IU/ml) diluted with a reaction buffer as attached at 37° C. for 5 min and successively washed with 0.1% SDS, 10 mM sodium hydroxide, and 10 mM hydrochloric acid each at 37° C. for 1 min to remove the ligase and the samples as well.

This solid phase was reacted with Exonuclease I (200 unit/ml; available from Amersham Inc.) diluted with a 67 mM glycine-sodium hydroxide buffer (pH 9.5) containing 10 mM 2-mercaptoethanol and 6.7 mM magnesium chloride at 37° C. for 20 min and further washed with a TE buffer for 30 min, when mass variations of the solid phase were observed with the surface plasmon resonance sensor. Although the decrease remained as small as 39 resonance units in the case where the target nucleic acid A was reacted, a decrease of as large as 131 resonance units was noted for Sequence A devoid of one base, 125 resonance units for the sequence with one extra base noted, and further 174 resonance units noted in the case where absolutely no target nucleic acid was allowed to act upon the solid phase.

This suggests that the immobilization method not forming a complex in advance can also recognize nucleic acids which differ to slight degrees from the nucleic acid to be detected. However, where the nucleic acid is reacted with the solid phase, a decrease in the mass of the solid phase ascribable to the digestion of unreacted probes is noted in a considerable number of cases, which makes it difficult to judge the results.

| | Solid phase mass variations (RU) | | |
| --- | --- | --- | --- |
| | Immobilization step | Hybridization step | Digestion step |
| Target nucleic acid A | 547 | 597 | −39 |
| No target nucleic acid | 513 | −7 | −174 |
| Sequence A devoid of one base | 521 | 624 | −131 |
| Sequence with one extra base | 484 | 609 | −125 |

EXAMPLE 9

Method of Forming a Complex

Probes A and B (each 400 nM), and the target nucleic acid A (400 nM) capable of retaining these probes in proximity with each other were mixed in 1×SSPE, the mixed solution was heated at 100° C. for 5 min to effect denaturation and thereafter, maintained at 55° C. for 10 min to effect hybridization, forming a complex.

The above-mentioned solution was charged on an ion-exchange high performance liquid chromatography column DNA-NPR (available from Toso Co. Ltd.), eluted with sodium chloride gradients containing a 20 mM Tris-HCl buffer and a major peak found in the vicinity of a sodium chloride concentration of 457 mM was fractionated to obtain a complex. The complex was reacted with the BIAcore sensor chip SA coated with streptavidin at 37° C. for 5 min, achieving its binding through the biotin-streptavidin binding. Thereafter, the solid phase was successively washed with 0.1% SDS, 10 mM sodium hydroxide, and 10 mM hydrochloric acid each at 37° C. for 1 min to remove the target nucleic acid A and to form a solid phase for the detection of any target nucleic acid.

When the above-mentioned solid phase for the detection of a target nucleic acid was reacted with samples at 37° C. for 10 min which had been diluted with 1×SSPE to provide 400 nM of respective sequences as described below, their mass variations were observed with the surface plasmon resonance sensor. Increases of 639~705 resonance units were noted.

The sequences that were used as samples are as follows:

```
Target Nucleic Acid A;
5'-GCAGCCCGGG GGATCCACTA GTTCTAGAGC GGCCGCCACC-3'
```

-continued

Sequence A devoid of one base;
5'-GCAGCCCGGG GGATCCACT GTTCTAGAGC GGCCGCCACC-3'

Sequence with one extra base;
5'-GCAGCCCGGG GGATCCACTAAG TTCTAGAGC GGCCGCCACC-3'

This solid phase was reacted with T4 DNA ligase (3500 IU/ml) diluted with a reaction buffer as attached at 37° C. for 5 min and successively washed with 0.1% SDS, 10 mM sodium hydroxide, and 10 mM hydrochloric acid each at 37° C. for 1 min to remove the ligase and the samples as well.

This solid phase was reacted with Exonuclease I (200 unit/ml) diluted with a 67 mM glycine-sodium hydroxide buffer (pH 9.5) containing 10 mM 2-mercaptoethanol and 6.7 mM magnesium chloride at 37° C. for 20 min and it was further washed with a TE buffer for 30 min, when mass variations of the solid phase were observed with the surface plasmon resonance sensor. Although the decrease remained as small as 7 resonance units in the case where the target nucleic acid A was reacted, a decrease of as large as 105 resonance units was noted for Sequence A devoid of one base, 113 resonance units for the sequence with one extra base noted, and further 160 resonance units noted in the case where absolutely no target nucleic acid was allowed to act upon the solid phase.

This suggests that with the use of the immobilization method for forming a complex in advance, the target sequence can be more clearly distinguished from other sequences.

|  | Solid phase mass variations (RU) | | |
| --- | --- | --- | --- |
|  | Immobilization step | Hybridization step | Digestion step |
| Target nucleic acid A | 471 | 705 | −7 |
| no target nucleic acid | 453 | −2 | −160 |
| Sequence A devoid of one base | 448 | 639 | −105 |
| Sequence with one extra base | 460 | 655 | −113 |

INDUSTRIAL APPLICABILITY

In accordance with this invention, solid phases for the detection of target nucleic acids based on the preparation methods of the solid phase for the detection of target nucleic acids and methods of detecting target nucleic acids employing said solid phases for the detection of target nucleic acids allow a wide variety of target nucleic acids in a sample to be simultaneously detected with ease, rapidity, and high accuracy as well as allows a large number of base sequence groups contained in target nucleic acids to be simultaneously detected with high accuracy.

What is claimed is:

1. A solid phase for the detection of a target nucleic acid comprising a pair of probes, wherein said pair of probes has a base sequence that sequentially hybridizes with a specified polynucleotide sequence of said target nucleic acid, and wherein one of the pair of probes is immobilized on said solid phase at the 5' end thereof through a first linker portion and the other of the pair of probes is immobilized on said solid phase at the 3' end thereof through a second linker portion in such a manner as to occupy a restricted spatial arrangement so that the probes are ligated by an enzyme when the probes sequentially hybridize with the specified polynucleotide sequence of said target nucleic acid.

2. The solid phase for the detection of a target nucleic acid according to claim 1, being produced by the step wherein one of the pair of probes is immobilized on said solid phase at the 5' end thereof through a first linker portion and the other of the pair of probes is immobilized on said solid phase at the 3' end thereof through a second linker portion in such a manner as to occupy a restricted spatial arrangement such that the solid phase hybridizes with the target nucleic acid to form a complex.

3. The solid phase for detection according to claim 1, wherein at least one of the pair of probes is further provided with a base sequence that hybridizes with a padlock probe.

4. A method of preparing a solid phase for the detection of a target nucleic acid, said method comprising the steps of:
   (1) hybridizing a pair of probes with the target nucleic acid to form a complex, said pair of probes having a base sequence that sequentially hybridizes with a specified polynucleotide sequence of said target nucleic acid;
   (2) immobilizing the pair of probes having formed the complex, on a surface of the solid phase through a linker portion; and
   (3) denaturing and removing said target nucleic acid to prepare a solid phase for the detection of a target nucleic acid.

5. The method of preparation according to claim 4, wherein the linker portion is formed by a binding reaction of biotin with avidin or streptavidin.

6. The method of preparation according to claim 4, wherein at least one of the pair of probes is further provided with a base sequence that hybridizes with a padlock probe.

7. A solid phase for detection being produced by the method of preparation according to claim 4.

8. A method of detecting a target nucleic acid comprising the steps of:
   (1) hybridizing a solid phase for the detection of a target nucleic acid with the target nucleic acid to form a complex, wherein said solid phase comprises a pair of probes, wherein said pair of probes has a base sequence that sequentially hybridizes with a specified polynucleotide sequence of said target nucleic acid, and wherein one of the pair of probes is immobilized on said solid phase at the 5' end thereof through a first linker portion and the other of the pair of probes is immobilized on said solid phase at the 3' end thereof through a second linker portion in such a manner as to occupy a restricted spatial arrangement so that the probes can be ligated by an enzyme when the probes sequentially hybridize with the specified polynucleotide sequence of said target nucleic acid;
   (2) ligating the pair of probes by a ligase reaction of the complex to form a ligation product; and
   (3) detecting the ligation product to detect a target nucleic acid.

9. The method of detection according to claim 8, wherein the ligation product is detected based on a resistance activity thereof against exonuclease digestion in the step for detection of the ligation product.

10. The method of detection according to claim 9, wherein the resistance activity of the ligation product against the exonuclease digestion is detected based on mass variations of the solid phase.

11. The method of detection according to claim 10, wherein the mass variations of the solid phase are based on fluctuations of reflective index as determined by a surface plasmon resonance sensor.

12. A method of detecting a target nucleic acid comprising the steps of:
   (1) hybridizing a solid phase for the detection of a target nucleic acid with the target nucleic acid to form a complex, wherein said solid phase comprises a pair of probes, wherein said pair of probes has a base sequence that sequentially hybridizes with a specified polynucleotide sequence of said target nucleic acid and a base sequence that hybridizes with a padlock probe, and wherein one of the pair of probes is immobilized on said solid phase at the 5' end thereof through a first linker portion and the other of the pair of probes is immobilized on said solid phase at the 3' end thereof through a second linker portion in such a manner as to occupy a restricted spatial arrangement so that the probes are ligated by an enzyme when the probes sequentially hybridize with the specified polynucleotide sequence of said target nucleic acid;
   (2) ligating the pair of probes by a ligase reaction of the complex to form a ligation product;
   (3) hybridizing the ligation product with the padlock probe;
   (4) ring-closing the padlock probe around the ligation product in a continuous loop by a ligase reaction; and
   (5) detecting the ring-closed padlock probe to detect a target nucleic acid.

* * * * *